(12) United States Patent
Eriksson et al.

(10) Patent No.: US 11,607,144 B2
(45) Date of Patent: Mar. 21, 2023

(54) SENSOR BASED CONTEXT MANAGEMENT (71) Applicant: Suunto Oy, Vantaa (FI)

(72) Inventors: Timo Eriksson, Vantaa (FI); Mikko Martikka, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 387 days.

(21) Appl. No.: 15/382,763

(22) Filed: Dec. 19, 2016

(65) Prior Publication Data
US 2017/0176213 A1    Jun. 22, 2017

(51) Int. Cl.
*H04W 4/70* (2018.01)
*A61B 5/0245* (2006.01)
*G16H 40/67* (2018.01)
*A61B 5/00* (2006.01)
*A61B 5/11* (2006.01)
*A61B 5/352* (2021.01)
*G06V 40/20* (2022.01)
*G01C 22/00* (2006.01)
(Continued)

(52) U.S. Cl.
CPC .......... *A61B 5/0245* (2013.01); *A61B 5/0006* (2013.01); *A61B 5/0022* (2013.01); *A61B 5/02438* (2013.01); *A61B 5/1118* (2013.01); *A61B 5/352* (2021.01); *A61B 5/681* (2013.01); *G01C 22/006* (2013.01); *G01P 15/0802* (2013.01); *G06V 40/23* (2022.01); *G16H 40/67* (2018.01); *A61B 5/7275* (2013.01); *A61B 2503/10* (2013.01)

(58) Field of Classification Search
CPC . G01C 22/006; G01P 15/0802; A61B 5/0006; A61B 5/02438
See application file for complete search history.

(56) References Cited

U.S. PATENT DOCUMENTS

| | | |
|---|---|---|
| 5,457,284 A | 10/1995 | Ferguson |
| 5,503,145 A | 4/1996 | Clough |
| 5,924,980 A | 7/1999 | Coetzee |

(Continued)

FOREIGN PATENT DOCUMENTS

| | | |
|---|---|---|
| AU | 2007216704 A1 | 4/2008 |
| CN | 1877340 A1 | 12/2006 |

(Continued)

OTHER PUBLICATIONS

ARM big. LITTLE. Wikipedia, The free encyclopedia, Oct. 11, 2018, Retrieved on May 28, 2020 from: <https://en.wikipedia.org/w/index.php?title=ARM_bit.LITTLE&oldid=863559211> foreword on p. 1, section "Run-state migration" on pp. 1-2.

(Continued)

*Primary Examiner* — Eyob Hagos
(74) *Attorney, Agent, or Firm* — Laine IP Oy (57) ABSTRACT

According to an example aspect of the present invention, there is provided an apparatus comprising a memory configured to store first-type sensor data, at least one processing core configured to compile a message based at least partly on the first-type sensor data, to cause the message to be transmitted from the apparatus, to cause receiving in the apparatus of a machine readable instruction, and to derive an estimated activity type, using the machine readable instruction, based at least partly on sensor data

25 Claims, 6 Drawing Sheets

(51) Int. Cl.
*G01P 15/08* (2006.01)
*A61B 5/024* (2006.01)

(56) References Cited

U.S. PATENT DOCUMENTS

| | | |
|---|---|---|
| 6,882,955 B1 | 4/2005 | Ohlenbusch et al. |
| 7,627,423 B2 | 12/2009 | Brooks |
| 7,706,973 B2 | 4/2010 | McBride et al. |
| 7,721,118 B1 | 5/2010 | Tamasi et al. |
| 7,917,198 B2 | 3/2011 | Ahola et al. |
| 7,938,752 B1 | 5/2011 | Wang |
| 8,052,580 B2 | 11/2011 | Saalasti et al. |
| 8,323,188 B2 | 12/2012 | Tran |
| 8,328,718 B2 | 12/2012 | Tran |
| 8,538,693 B2 | 9/2013 | McBride et al. |
| 8,612,142 B2 | 12/2013 | Zhang |
| 8,655,591 B2 | 2/2014 | Van Hende |
| 8,781,730 B2 | 7/2014 | Downey et al. |
| 8,949,022 B1 | 2/2015 | Fahrner et al. |
| 9,008,967 B2 | 4/2015 | McBride et al. |
| 9,079,090 B2 * | 7/2015 | Hohteri ............ H04M 1/72409 |
| 9,107,586 B2 | 8/2015 | Tran |
| 9,222,787 B2 | 12/2015 | Blumenberg et al. |
| 9,317,660 B2 | 4/2016 | Burich et al. |
| 9,595,187 B2 * | 3/2017 | Kotz .................. A61B 5/1118 |
| 9,648,108 B2 | 5/2017 | Granqvist et al. |
| 9,665,873 B2 | 5/2017 | Ackland et al. |
| 9,829,331 B2 | 11/2017 | McBride et al. |
| 9,830,516 B1 | 11/2017 | Biswas et al. |
| 9,907,473 B2 | 3/2018 | Tran |
| 9,923,973 B2 | 3/2018 | Granqvist et al. |
| 10,234,290 B2 | 3/2019 | Lush et al. |
| 10,244,948 B2 | 4/2019 | Pham et al. |
| 10,295,556 B1 | 5/2019 | Paczkowski et al. |
| 10,327,673 B2 | 6/2019 | Eriksson et al. |
| 10,415,990 B2 | 9/2019 | Cho et al. |
| 10,433,768 B2 | 10/2019 | Eriksson et al. |
| 10,515,990 B2 | 12/2019 | Hung et al. |
| 10,634,511 B2 | 4/2020 | McBride et al. |
| 10,816,671 B2 | 10/2020 | Graham et al. |
| 2003/0038831 A1 | 2/2003 | Engelfriet |
| 2003/0109287 A1 | 6/2003 | Villaret |
| 2005/0070809 A1 | 3/2005 | Acres |
| 2005/0086405 A1 | 4/2005 | Kobayashi et al. |
| 2006/0068812 A1 | 3/2006 | Carro et al. |
| 2006/0136173 A1 | 6/2006 | Case, Jr. et al. |
| 2006/0255963 A1 | 11/2006 | Thompson et al. |
| 2007/0156335 A1 | 7/2007 | McBride et al. |
| 2007/0208544 A1 | 9/2007 | Kulach et al. |
| 2007/0276200 A1 | 11/2007 | Ahola et al. |
| 2008/0052493 A1 | 2/2008 | Chang |
| 2008/0109158 A1 | 5/2008 | Huhtala et al. |
| 2008/0136620 A1 | 6/2008 | Lee et al. |
| 2008/0158117 A1 | 7/2008 | Wong et al. |
| 2008/0214360 A1 | 9/2008 | Stirling et al. |
| 2008/0294663 A1 | 11/2008 | Heinley et al. |
| 2008/0318598 A1 | 12/2008 | Fry |
| 2009/0047645 A1 | 2/2009 | DiBenedetto et al. |
| 2009/0048070 A1 | 2/2009 | Vincent et al. |
| 2009/0094557 A1 | 4/2009 | Howard |
| 2009/0100332 A1 | 4/2009 | Kanjilal et al. |
| 2009/0265623 A1 | 10/2009 | Kho et al. |
| 2010/0099539 A1 | 4/2010 | Haataja |
| 2010/0167712 A1 | 7/2010 | Stallings et al. |
| 2010/0187074 A1 | 7/2010 | Manni |
| 2010/0257014 A1 | 10/2010 | Roberts et al. |
| 2010/0313042 A1 | 12/2010 | Shuster |
| 2011/0010704 A1 | 1/2011 | Jeon et al. |
| 2011/0152695 A1 | 6/2011 | Granqvist et al. |
| 2011/0218385 A1 | 9/2011 | Bolyard et al. |
| 2011/0251822 A1 | 10/2011 | Darley et al. |
| 2011/0252351 A1 | 10/2011 | Sikora et al. |
| 2011/0281687 A1 | 11/2011 | Gilley et al. |
| 2011/0283224 A1 | 11/2011 | Ramsey et al. |
| 2011/0288381 A1 | 11/2011 | Bartholomew et al. |
| 2011/0296312 A1 | 12/2011 | Boyer et al. |
| 2011/0307723 A1 | 12/2011 | Cupps et al. |
| 2012/0022336 A1 | 1/2012 | Teixeira |
| 2012/0100895 A1 | 4/2012 | Priyantha et al. |
| 2012/0109518 A1 | 5/2012 | Huang |
| 2012/0116548 A1 | 5/2012 | Goree et al. |
| 2012/0123806 A1 | 5/2012 | Schumann et al. |
| 2012/0158289 A1 | 6/2012 | Bernheim Brush et al. |
| 2012/0185268 A1 | 7/2012 | Wiesner et al. |
| 2012/0219186 A1 | 8/2012 | Wang et al. |
| 2012/0239173 A1 | 9/2012 | Laikari et al. |
| 2012/0283855 A1 | 11/2012 | Hoffman et al. |
| 2012/0289791 A1 | 11/2012 | Jain et al. |
| 2012/0317520 A1 | 12/2012 | Lee |
| 2013/0053990 A1 | 2/2013 | Ackland et al. |
| 2013/0060167 A1 * | 3/2013 | Dracup ................ A61B 5/0022 600/595 |
| 2013/0095459 A1 | 4/2013 | Tran |
| 2013/0127636 A1 | 5/2013 | Aryanpur et al. |
| 2013/0151874 A1 | 6/2013 | Parks et al. |
| 2013/0166888 A1 | 6/2013 | Branson et al. |
| 2013/0178334 A1 | 7/2013 | Brammer |
| 2013/0187789 A1 | 7/2013 | Lowe et al. |
| 2013/0190903 A1 | 7/2013 | Balakrishnan et al. |
| 2013/0217979 A1 | 8/2013 | Blackadar et al. |
| 2013/0225370 A1 | 8/2013 | Flynt et al. |
| 2013/0234924 A1 | 9/2013 | Janefalkar et al. |
| 2013/0250845 A1 | 9/2013 | Greene et al. |
| 2013/0289932 A1 * | 10/2013 | Baechler ............ G01P 15/0891 702/141 |
| 2013/0304377 A1 | 11/2013 | Van Hende |
| 2013/0312043 A1 | 11/2013 | Stone et al. |
| 2013/0332286 A1 | 12/2013 | Medelius et al. |
| 2013/0345978 A1 | 12/2013 | Lush et al. |
| 2014/0018686 A1 | 1/2014 | Medelius et al. |
| 2014/0046223 A1 * | 2/2014 | Kahn .................. A61B 5/1038 600/595 |
| 2014/0094200 A1 | 4/2014 | Schatzberg et al. |
| 2014/0135593 A1 | 5/2014 | Jayalth et al. |
| 2014/0142732 A1 | 5/2014 | Karvonen |
| 2014/0149754 A1 | 5/2014 | Silva et al. |
| 2014/0159915 A1 | 6/2014 | Hong et al. |
| 2014/0163927 A1 | 6/2014 | Molettiere et al. |
| 2014/0208333 A1 | 7/2014 | Beals et al. |
| 2014/0218281 A1 | 8/2014 | Amayeh et al. |
| 2014/0235166 A1 | 8/2014 | Molettiere et al. |
| 2014/0237028 A1 | 8/2014 | Messenger et al. |
| 2014/0257533 A1 | 9/2014 | Morris et al. |
| 2014/0275821 A1 | 9/2014 | Beckman |
| 2014/0288680 A1 | 9/2014 | Hoffman et al. |
| 2014/0300490 A1 * | 10/2014 | Kotz ...................... G16H 40/67 340/870.3 |
| 2014/0336796 A1 | 11/2014 | Agnew |
| 2014/0337036 A1 | 11/2014 | Haiut et al. |
| 2014/0337450 A1 | 11/2014 | Choudhary et al. |
| 2014/0343380 A1 | 11/2014 | Carter et al. |
| 2014/0350883 A1 | 11/2014 | Carter et al. |
| 2014/0365107 A1 | 12/2014 | Dutta et al. |
| 2014/0372064 A1 | 12/2014 | Darley et al. |
| 2015/0006617 A1 * | 1/2015 | Yoo ........................ H04L 67/12 709/203 |
| 2015/0037771 A1 | 2/2015 | Kaleal, III et al. |
| 2015/0042468 A1 | 2/2015 | White et al. |
| 2015/0057945 A1 | 2/2015 | White et al. |
| 2015/0113417 A1 | 4/2015 | Yuen et al. |
| 2015/0119198 A1 | 4/2015 | Wisbey et al. |
| 2015/0119728 A1 | 4/2015 | Blackadar et al. |
| 2015/0127966 A1 | 5/2015 | Ma et al. |
| 2015/0141873 A1 | 5/2015 | Fei |
| 2015/0160026 A1 | 6/2015 | Kitchel |
| 2015/0180842 A1 | 6/2015 | Panther |
| 2015/0185815 A1 | 7/2015 | Debates et al. |
| 2015/0209615 A1 | 7/2015 | Edwards |
| 2015/0233595 A1 | 8/2015 | Fadell et al. |
| 2015/0272483 A1 | 10/2015 | Etemad et al. |
| 2015/0312857 A1 | 10/2015 | Kim et al. |
| 2015/0317801 A1 | 11/2015 | Bentley et al. |
| 2015/0326709 A1 | 11/2015 | Pennanen et al. |
| 2015/0334772 A1 | 11/2015 | Wong et al. |

(56) References Cited

U.S. PATENT DOCUMENTS

| | | |
|---|---|---|
| 2015/0335978 A1 | 11/2015 | Syed et al. |
| 2015/0342533 A1 | 12/2015 | Kelner |
| 2015/0347983 A1 | 12/2015 | Jon et al. |
| 2015/0350822 A1 | 12/2015 | Xiao et al. |
| 2015/0362519 A1 | 12/2015 | Balakrishnan et al. |
| 2015/0374279 A1 | 12/2015 | Takakura et al. |
| 2015/0382150 A1 | 12/2015 | Ansermet et al. |
| 2016/0007288 A1 | 1/2016 | Samardzija et al. |
| 2016/0007934 A1* | 1/2016 | Arnold .............. A61B 5/02055 600/595 |
| 2016/0012294 A1 | 1/2016 | Bouck |
| 2016/0018899 A1 | 1/2016 | Tu et al. |
| 2016/0023043 A1 | 1/2016 | Grundy |
| 2016/0026236 A1 | 1/2016 | Vasistha et al. |
| 2016/0034043 A1 | 2/2016 | Le Grand et al. |
| 2016/0034133 A1 | 2/2016 | Wilson et al. |
| 2016/0041593 A1 | 2/2016 | Dharawat |
| 2016/0058367 A1 | 3/2016 | Raghuram et al. |
| 2016/0058372 A1 | 3/2016 | Raghuram et al. |
| 2016/0059079 A1 | 3/2016 | Watterson |
| 2016/0072557 A1 | 3/2016 | Ahola |
| 2016/0081028 A1 | 3/2016 | Chang et al. |
| 2016/0081625 A1 | 3/2016 | Kim et al. |
| 2016/0084869 A1 | 3/2016 | Yuen et al. |
| 2016/0091980 A1 | 3/2016 | Baranski et al. |
| 2016/0104377 A1 | 4/2016 | French et al. |
| 2016/0105852 A1 | 4/2016 | Papakipos et al. |
| 2016/0135698 A1 | 5/2016 | Baxi et al. |
| 2016/0143579 A1 | 5/2016 | Martikka et al. |
| 2016/0144236 A1 | 5/2016 | Ko et al. |
| 2016/0148396 A1 | 5/2016 | Bayne et al. |
| 2016/0148615 A1 | 5/2016 | Lee et al. |
| 2016/0184686 A1 | 6/2016 | Sampathkumaran |
| 2016/0209907 A1 | 7/2016 | Han et al. |
| 2016/0226945 A1 | 8/2016 | Granqvist et al. |
| 2016/0259495 A1 | 9/2016 | Butcher et al. |
| 2016/0317097 A1 | 11/2016 | Adams et al. |
| 2016/0327915 A1 | 11/2016 | Katzer et al. |
| 2016/0328991 A1 | 11/2016 | Simpson et al. |
| 2016/0346611 A1 | 12/2016 | Rowley et al. |
| 2016/0357202 A1 | 12/2016 | Carter et al. |
| 2016/0374566 A1 | 12/2016 | Fung et al. |
| 2016/0379547 A1 | 12/2016 | Okada |
| 2017/0010677 A1 | 1/2017 | Roh et al. |
| 2017/0011089 A1 | 1/2017 | Bermudez et al. |
| 2017/0011210 A1 | 1/2017 | Cheong et al. |
| 2017/0032256 A1 | 2/2017 | Otto et al. |
| 2017/0038740 A1 | 2/2017 | Knappe et al. |
| 2017/0043212 A1* | 2/2017 | Wong .................. G06V 40/23 |
| 2017/0063475 A1 | 3/2017 | Feng |
| 2017/0065230 A1 | 3/2017 | Sinha et al. |
| 2017/0087431 A1 | 3/2017 | Syed et al. |
| 2017/0124517 A1 | 5/2017 | Martin |
| 2017/0153119 A1 | 6/2017 | Nieminen et al. |
| 2017/0153693 A1 | 6/2017 | Duale et al. |
| 2017/0154270 A1 | 6/2017 | Lindman et al. |
| 2017/0168555 A1 | 6/2017 | Munoz et al. |
| 2017/0173391 A1 | 6/2017 | Wiebe et al. |
| 2017/0232294 A1 | 8/2017 | Kruger et al. |
| 2017/0262699 A1 | 9/2017 | White et al. |
| 2017/0266494 A1 | 9/2017 | Crankson et al. |
| 2017/0316182 A1 | 11/2017 | Blackadar et al. |
| 2017/0340221 A1* | 11/2017 | Cronin .............. G08B 21/0211 |
| 2018/0015329 A1 | 1/2018 | Burich et al. |
| 2018/0108323 A1 | 4/2018 | Lindman et al. |
| 2018/0193695 A1 | 7/2018 | Lee |
| 2018/0345077 A1 | 12/2018 | Blahnik et al. |
| 2019/0025928 A1 | 1/2019 | Pantelopoulos et al. |
| 2019/0056777 A1 | 2/2019 | Munoz et al. |
| 2019/0069244 A1 | 2/2019 | Jeon et al. |
| 2019/0367143 A1 | 12/2019 | Sinclair et al. |

FOREIGN PATENT DOCUMENTS

| | | |
|---|---|---|
| CN | 102495756 A | 6/2012 |
| CN | 103309428 A | 9/2013 |
| CN | 103631359 A | 3/2014 |
| CN | 103970271 A | 8/2014 |
| CN | 204121706 U | 1/2015 |
| CN | 104680046 A | 6/2015 |
| CN | 105242779 A1 | 1/2016 |
| CN | 106062661 A | 10/2016 |
| CN | 106604369 A | 4/2017 |
| CN | 106999106 A | 8/2017 |
| CN | 108052272 A | 5/2018 |
| CN | 103154954 B | 6/2018 |
| CN | 108377264 A | 8/2018 |
| CN | 108983873 A | 12/2018 |
| EP | 1755098 A2 | 2/2007 |
| EP | 2096820 A1 | 9/2009 |
| EP | 2107837 A1 | 10/2009 |
| EP | 2172249 A2 | 4/2010 |
| EP | 2770454 A1 | 8/2014 |
| EP | 2703945 A2 | 3/2015 |
| EP | 2849473 A1 | 3/2015 |
| EP | 2910901 A1 | 8/2015 |
| EP | 2996409 A1 | 3/2016 |
| EP | 3018582 A2 | 5/2016 |
| EP | 3023859 A1 | 5/2016 |
| EP | 3361370 A | 8/2018 |
| FI | 126911 B | 2/2017 |
| GB | 2404593 A | 2/2005 |
| GB | 2425180 A | 10/2006 |
| GB | 2513585 A | 11/2014 |
| GB | 2530196 A | 3/2016 |
| GB | 2537423 A | 10/2016 |
| GB | 2541234 A | 2/2017 |
| GB | 2555107 A | 4/2018 |
| KR | 20110070049 A | 6/2011 |
| KR | 101500662 B1 | 3/2015 |
| SE | 528295 C2 | 10/2006 |
| TW | 201706840 A | 2/2017 |
| TW | I598076 A | 9/2018 |
| WO | WO02054157 A1 | 7/2002 |
| WO | WO2010083562 A1 | 7/2010 |
| WO | WO2010144720 A1 | 12/2010 |
| WO | WO 2011061412 A1 | 5/2011 |
| WO | WO2011123932 A1 | 10/2011 |
| WO | WO2012037637 A1 | 3/2012 |
| WO | WO2012115943 A1 | 8/2012 |
| WO | WO2012141827 A2 | 10/2012 |
| WO | WO2013091135 A1 | 6/2013 |
| WO | WO2013121325 A2 | 8/2013 |
| WO | WO2014118767 A1 | 8/2014 |
| WO | WO2014144258 A2 | 9/2014 |
| WO | WO2014193672 A1 | 12/2014 |
| WO | WO 2014209697 A1 | 12/2014 |
| WO | WO 2015021407 A1 | 2/2015 |
| WO | WO2014182162 A3 | 6/2015 |
| WO | WO2015087164 A1 | 6/2015 |
| WO | WO2015131065 A1 | 9/2015 |
| WO | WO2016022203 A1 | 2/2016 |
| WO | WO2017011818 A1 | 1/2017 |
| WO | WO2018217348 A1 | 11/2018 |
| WO | WO2018222936 A1 | 12/2018 |

OTHER PUBLICATIONS

Qualcomm Snapdragon Wear 3100 Platform Supports New Ultra-Low Power System Architecture For Next Generation Smartwatches. Qualcomm Technologies, Inc., Sep. 10, 2018, Retrieved on May 28, 2018 from: <https://www.qualcomm.com/news/releases/2018/09/10/qualcomm-snapdragon-wear-3100-platform-supports-sections "Snapdragon Wear 3100 Based Smartwatches Aim to Enrich the User Experience" on pp. 3-4.

Sheta et al: Packet scheduling in LTE mobile network. International Journal of Scientific & Engineering Research, Jun. 2013, vol. 4, Issue 6.

(56) References Cited

OTHER PUBLICATIONS

CNET: Dec. 11, 2017, "Apple watch can now sync with a treadmill", youtube.com, [online], Available from: https://www.youtube.com/watch?v=7RvMC3wFDME [ Accessed Nov. 19, 2020].
CASH: A guide to GPS and route plotting for cyclists. 2018. www.cyclinguk.org/article/guide-gps-and-route-plotting-cyclists.
Sieber et al.: Embedded systems in the Poseidon MK6 rebreather. Intelligent Solutions in Embedded Systems, 2009, pp. 37-42.
Ainsworth et al: Parallel Error Detection Using Heterogeneous Cores. 48th Annual IEEE/IFIP International Conference on Dependable Systems and Networks (DSN), 2018, IEEE, 2018.
DAVIS: The Best Technical Diving Computers 2019. Feb. 7, 2019.

\* cited by examiner

SENSOR BASED CONTEXT MANAGEMENT

FIELD

The present invention relates to identification of user activity based on sensor information.

BACKGROUND

User sessions, such as training sessions, may be recorded, for example in notebooks, spreadsheets or other suitable media. Recorded training sessions enable more systematic training, and progress toward set goals can be assessed and tracked from the records so produced. Such records may be stored for future reference, for example to assess progress an individual is making as a result of the training. An activity session may comprise a training session or another kind of session.

Personal devices, such as, for example, smart watches, smartphones or smart jewellery, may be configured to produce recorded sessions of user activity. Such recorded sessions may be useful in managing physical training, child safety or in professional uses. Recorded sessions, or more generally sensor-based activity management, may be of varying type, such as, for example, running, walking, skiing, canoeing, wandering, or assisting the elderly.

Recorded sessions may be viewed using a personal computer, for example, wherein recordings may be copied from a personal device to the personal computer. Files on a personal computer may be protected using passwords and/or encryption, for example.

Personal devices may be furnished with sensors, which may be used, for example, in determining a location of the personal device. For example, a satellite positioning sensor may receive positioning information from a satellite constellation, and deduce therefrom where the personal device is located. A recorded training session may comprise a route determined by repeatedly determining the location of the personal device during the training session. Such a route may be later observed using a personal computer, for example.

Alternatively to a satellite positioning sensor, a personal device may be configured to determine its location using, for example, a cellular network based location determining method, wherein a cellular network is used to assist determination of the location. For example, a cell that maintains attachment of the personal device to the cellular network may have a known location, providing a location estimate of the personal device owing to the attachment and a finite geographic extent of the cell.

SUMMARY OF THE INVENTION

The invention is defined by the features of the independent claims. Some specific embodiments are defined in the dependent claims.

According to a first aspect of the present invention, there is provided an apparatus comprising a memory configured to store first-type sensor data, at least one processing core configured to compile a message based at least partly on the first-type sensor data, to cause the message to be transmitted from the apparatus, to cause receiving in the apparatus of a machine readable instruction, and to derive an estimated activity type, using the machine readable instruction, based at least partly on sensor data.

Various embodiments of the first aspect may comprise at least one feature from the following bulleted list:

- the machine readable instruction comprises at least one of the following: an executable program, an executable script and a set of at least two machine-readable characteristics, wherein each of the characteristics characterizes sensor data produced during a predefined activity type
- the at least one processing core is configured to derive the estimated activity type at least in part by comparing, using the machine readable instruction, the first-type sensor data, or a processed form of the first-type sensor data, to reference data
- the first-type sensor data comprises acceleration sensor data
- the memory is further configured to store second-type sensor data, and wherein the at least one processing core is configured to derive the estimated activity type, using the machine readable instruction, based at least in part on the second-type sensor data
- the second-type sensor data is of a different type than the first-type sensor data
- the second-type sensor data comprises at least one of: sound sensor data, microphone-derived data and vibration sensor data
- the at least one processing core is configured to derive the estimated activity type at least in part by comparing the second-type sensor data, or a processed form of the second-type sensor data, to reference data, the reference data comprising reference data of a first type and a second type
- the at least one processing core is configured to present the estimated activity type to a user for verification
- the at least one processing core is configured to cause the memory to store, in a sequence of estimated activity types, the estimated activity type and a second estimated activity type
- the at least one processing core is configured to cause the memory to delete the machine readable instruction responsive to a determination that an activity session has ended.

According to a second aspect of the present invention, there is provided an apparatus comprising at least one processing core, at least one memory including computer program code, the at least one memory and the computer program code being configured to, with the at least one processing core, cause the apparatus at least to receive a message from a user device, the message comprising information characterizing first-type sensor data, determine, based at least partly on the first-type sensor data, an activity context, and transmit to the user device a machine-readable instruction configured to cause activity type determination in the activity context.

According to a third aspect of the present invention, there is provided a method, comprising storing first-type sensor data in an apparatus, compiling a message based at least partly on the first-type sensor data, causing the message to be transmitted from the apparatus, causing receiving in the apparatus of a machine readable instruction, and deriving an estimated activity type, using the machine readable instruction, based at least partly on sensor data.

Various embodiments of the third aspect may comprise at least one feature corresponding to a feature in the preceding bulleted list laid out in connection with the first aspect.

According to a fourth aspect of the present invention, there is provided a method, comprising receiving a message from a user device, the message comprising information characterizing first-type sensor data, determining, based at least partly on the first-type sensor data, an activity context, and transmitting to the user device a machine-readable instruction configured to cause activity type determination in the activity context.

According to a fifth aspect of the present invention, there is provided an apparatus comprising means for storing first-type sensor data in an apparatus, means for compiling a message based at least partly on the first-type sensor data, means for causing the message to be transmitted from the apparatus, means for causing receiving in the apparatus of a machine readable instruction, and means for deriving an estimated activity type, using the machine readable instruction, based at least partly on sensor data.

According to a sixth aspect of the present invention, there is provided a non-transitory computer readable medium having stored thereon a set of computer readable instructions that, when executed by at least one processor, cause an apparatus to at least store first-type sensor data, compile a message based at least partly on the first-type sensor data, cause the message to be transmitted from the apparatus, cause receiving in the apparatus of a machine readable instruction, and derive an estimated activity type, using the machine readable instruction, based at least partly on sensor data.

According to a seventh aspect of the present invention, there is provided a computer program configured to cause a method in accordance with at least one of the third and fourth aspects to be performed.

EMBODIMENTS

Employing sensor data to determine an activity type enhances usability of personal devices. For example, a user may be partly disabled, rendering his use of a device unassisted more difficult. Employing sensor data from more than one sensor may further enhance the accuracy of activity type estimation. To empower a reduced-capability user device to determine an activity type, a machine-readable instruction may be selected for, and provided to, the user device, by a back-end server. The selecting may be based on sensor data collected by the user device, such that the machine-readable instruction enables the user device to derive an estimated activity type in the user context where the user device is. Thus the derivation is partly performed in the back-end server, enabling the user device to provide a good estimation using only limited processor, energy and/or memory resources.

Figure 1:
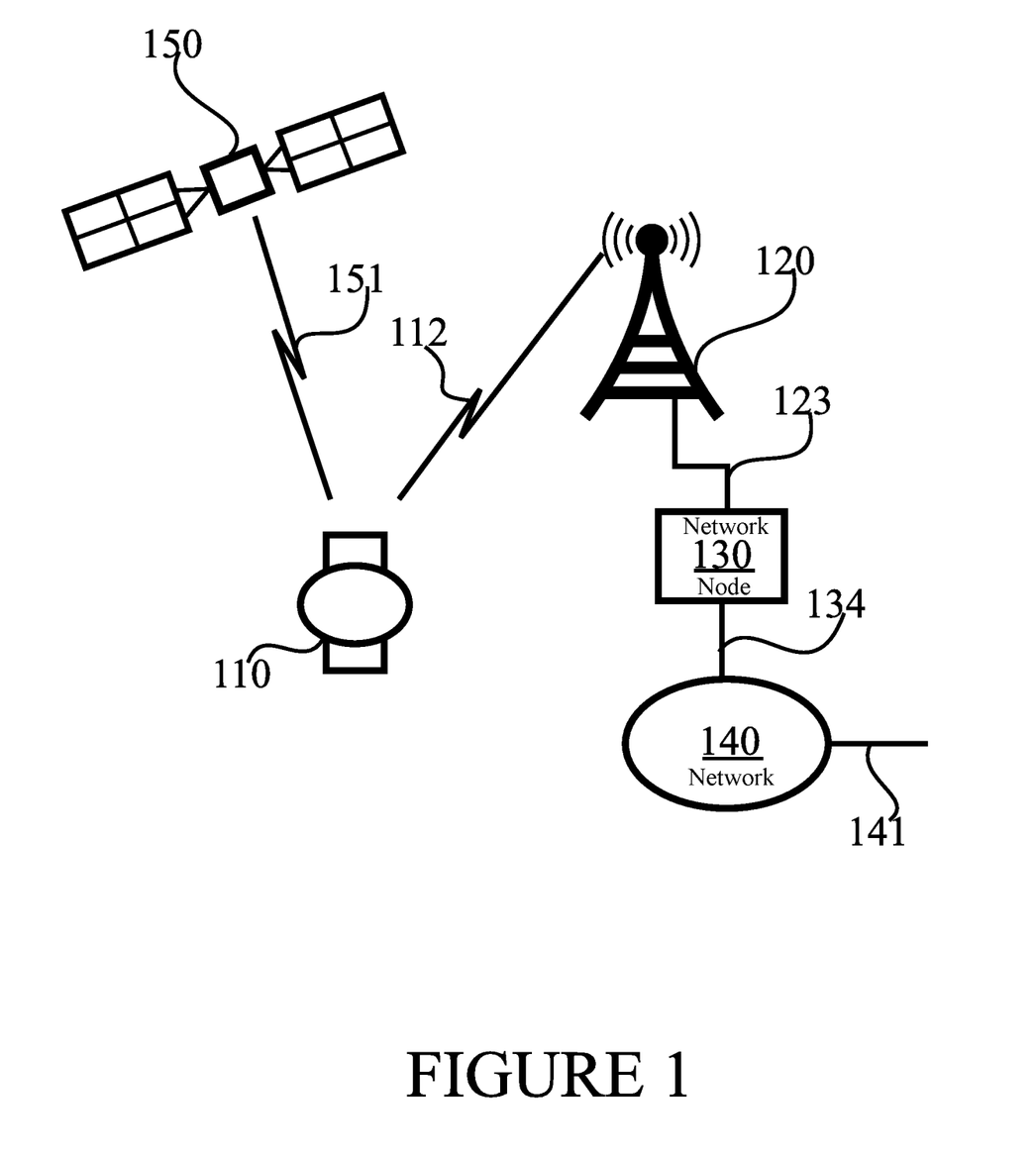
FIG. 1 illustrates an example system in accordance with at least some embodiments of the present invention.

FIG. 1 illustrates an example system in accordance with at least some embodiments of the present invention. The system comprises device 110, which may comprise, for example, a smart watch, digital watch, smartphone, phablet device, tablet device, or another type of suitable device. Device 110 may comprise a display, which may comprise a touchscreen display, for example. The display may be limited in size. Device 110 may be powered, for example, by a rechargeable battery. An example of a limited-size display is a display worn on a wrist.

Device 110 may be communicatively coupled with a communications network. For example, in FIG. 1 device 110 is coupled, via wireless link 112, with base station 120. Base station 120 may comprise a cellular or non-cellular base station, wherein a non-cellular base station may be referred to as an access point. Examples of cellular technologies include wideband code division multiple access, WCDMA, and long term evolution, LTE, while examples of non-cellular technologies include wireless local area network, WLAN, and worldwide interoperability for microwave access, WiMAX. Base station 120 may be coupled with network node 130 via connection 123. Connection 123 may be a wire-line connection, for example. Network node 130 may comprise, for example, a controller or gateway device. Network node 130 may interface, via connection 134, with network 140, which may comprise, for example, the Internet or a corporate network. Network 140 may be coupled with further networks via connection 141. In some embodiments, device 110 is not configured to couple with base station 120. Network 140 may comprise, or be communicatively coupled, with a back-end server, for example.

Device 110 may be configured to receive, from satellite constellation 150, satellite positioning information via satellite link 151. The satellite constellation may comprise, for example the global positioning system, GPS, or the Galileo constellation. Satellite constellation 150 may comprise more than one satellite, although only one satellite is illustrated in FIG. 1 for the same of clarity. Likewise, receiving the positioning information over satellite link 151 may comprise receiving data from more than one satellite.

Alternatively or additionally to receiving data from a satellite constellation, device 110 may obtain positioning information by interacting with a network in which base station 120 is comprised. For example, cellular networks may employ various ways to position a device, such as trilateration, multilateration or positioning based on an identity of a base station with which attachment is possible or ongoing. Likewise a non-cellular base station, or access point, may know its own location and provide it to device 110, enabling device 110 to position itself within communication range of this access point.

Device 110 may be configured to obtain a current time from satellite constellation 150, base station 120 or by requesting it from a user, for example. Once device 110 has the current time and an estimate of its location, device 110 may consult a look-up table, for example, to determine a time remaining until sunset or sunrise, for example. Device 110 may likewise gain knowledge of the time of year.

Device 110 may comprise, or be coupled with, at least one sensor, such as, for example, an acceleration sensor, moisture sensor, temperature sensor, heart rate sensor or a blood oxygen level sensor. Device 110 may be configured to produce and store, using the at least one sensor, sensor data, for example in a time series that comprises a plurality of samples taken in a time sequence.

Device 110 may be configured to provide an activity session. An activity session may be associated with an activity type. Examples of activity types include rowing, paddling, cycling, jogging, walking, hunting, swimming and paragliding. In a simple form, an activity session may comprise device 110 storing sensor data produced with sensors comprised in device 110, or in another device with which device 110 is associated or paired. An activity session may be determined to have started and ended at certain points in time, such that the determination takes place afterward or concurrently with the starting and/or ending. In other words, device 110 may store sensor data to enable subsequent identification of activity sessions based at least partly on the stored sensor data.

An activity session in device 110 may enhance a utility a user can obtain from the activity, for example, where the activity involves movement outdoors, the activity session may provide a recording of the activity session. Device 110 may, in some embodiments, provide the user with contextual information. Such contextual information may comprise, for example, locally relevant weather information, received via base station 120, for example. Such contextual information may comprise at least one of the following: a rain warning, a temperature warning, an indication of time remaining before sunset, an indication of a nearby service that is relevant to the activity, a security warning, an indication of nearby users and an indication of a nearby location where several other users have taken photographs. Contextual information may be presented during an activity session.

A recording of an activity session may comprise information on at least one of the following: a route taken during the activity session, a metabolic rate or metabolic effect of the activity session, a time the activity session lasted, a quantity of energy consumed during the activity session, a sound recording obtained during the activity session and an elevation map along the length of the route taken during the activity session. A route may be determined based on positioning information, for example. Metabolic effect and consumed energy may be determined, at least partly, based on information concerning the user that device 110 has access to. A recording may be stored in device 110, an auxiliary device, or in a server or data cloud storage service. A recording stored in a server or cloud may be encrypted prior to transmission to the server or cloud, to protect privacy of the user. A recording may be produced even if the user has not indicated an activity session has started, since a beginning and ending of an activity session may be determined after the session has ended, for example based, at least partly, on sensor data.

Device 110 may have access to a backhaul communications link to provide indications relating to ongoing activity. For example, search and rescue services may be given access to information on joggers in a certain area of a forest, to enable their rescue if a chemical leak, for example, makes the forest unsafe for humans. Alternatively or additionally, further users may be enabled to receive information on ongoing activity sessions. Such further users may be pre-configured as users who are cleared to receive such information, with non-cleared users not being provided such information, for example. As a specific example, users on a friend list may be able to obtain information on an ongoing activity session. The friend list may be maintained in a social media service, for example. The information on the ongoing activity session may be provided from device 110 as periodic updates, for example.

After an activity has ended, device 110 may have stored therein, or in a memory to which device 110 has access, sensor data. The stored sensor data may be stored as a time series that spans the activity session as well as time preceding and/or succeeding the activity session. The beginning and ending points in time of the activity session may be selected from the time series by the user. The beginning and ending points may be pre-selected by device 110, or a personal computer, for a user to accept or reject, the pre-selecting being based on changes in the time series. For example, where, in the time series, acceleration sensor data begins to indicate more active movements of device 110, a beginning point of an activity session may be pre-selected. Such a change may correspond to a time in the time series when the user stopped driving a car and began jogging, for example. Likewise, a phase in the time series where the more active movements end may be pre-selected as an ending point of the activity session.

Sensor data may comprise information from more than one sensor, wherein the more than one sensor may comprise sensors of at least two distinct types. For example, sensor data may comprise acceleration sensor data and air pressure sensor data. Further examples are sound volume sensor data, moisture sensor data and electromagnetic sensor data. In general sensor data from a sensor of a first type may be referred to as first-type sensor data, and sensor data from a sensor of a second type may be referred to as second-type sensor data. A type of a sensor may be defined by a physical property the sensor is configured to measure. For example, all temperature sensors may be considered temperature-type sensors, regardless of the physical principle used to measure temperature in the temperature sensor.

Pre-selecting the beginning and/or ending points in the time series may comprise detecting that sensor data characteristics of more than one sensor type changes at approximately the same phase of the time series. Using more than one type of sensor data may enhance the accuracy of beginning and/or ending time point pre-selection, in case the sensors in question are affected by the activity performed during the activity session.

An activity type may be determined based, at least partly, on the sensor data. This determining may take place when the activity is occurring, or afterwards, when analysing the sensor data. The activity type may be determined by device 110 or by a personal computer that has access to the sensor data, for example, or a server that is provided access to the sensor data. Where a server is given access to the sensor data, the sensor data may be anonymized. The determination of the activity type may comprise comparing the sensor data to reference data. The reference data may comprise reference datasets, each reference dataset being associated with an activity type. The determination may comprise determining the reference dataset that most resembles the sensor data, for example in a least-squares sense. Alternatively to the sensor data itself, a processed form of the sensor data may be compared to the reference data. The processed form may comprise, for example, a frequency spectrum obtained from the sensor data. Alternatively, the processed form may comprise a set of local minima and/or maxima from the sensor data time series. The determined activity type may be selected as the activity type associated with the reference dataset that most resembles the processed or original sensor data.

Different activity types may be associated with different characteristic frequencies. For example, acceleration sensor data may reflect a higher characteristic frequency when the user has been running, as opposed to walking. Thus the determination of activity type may be based, in some embodiments, at least partly, on deciding which reference dataset has a characteristic frequency that most closely matches a characteristic frequency of a section of the sensor-derived information time series under investigation. Alternatively or in addition, acceleration sensor data may be employed to determine a characteristic movement amplitude.

Where device 110 is configured to store a time series of more than one type of sensor data, plural sensor data types may be employed in determining the activity type. The reference data may comprise reference datasets that are multi-sensorial in nature in such a way, that each reference dataset comprises data that may be compared to each sensor data type that is available. For example, where device 110 is configured to compile a time series of acceleration and sound sensor data types, the reference data may comprise reference datasets, each reference dataset corresponding to an activity type, wherein each reference dataset comprises data that may be compared with the acceleration data and data that may be compared with the sound data. The determined activity type may be determined as the activity type that is associated with the multi-sensorial reference dataset that most closely matches the sensor data stored by device 110. Again, original or processed sensor data may be compared to the reference datasets. Where device 110 comprises, for example, a smartphone, it may comprise plural sensors to accomplish the smartphone function. Examples of such sensors comprise microphones to enable voice calls and cameras to enable video calls. Furthermore a radio receiver may, in some cases, be configurable to measure electric or magnetic field properties. Device 110 may comprise a radio receiver, in general, where device 110 is furnished with a wireless communication capability.

A first example of multi-sensorial activity type determination is hunting, wherein device 110 stores first-type sensor data that comprises acceleration sensor data and second-type sensor data that comprises sound data. The reference data would comprise a hunting reference dataset, which would comprise acceleration reference data and sound reference data, to enable comparison with sensor data stored by device 110. Hunting may involve periods of low sound and low acceleration and intermittent combinations of loud, short sound and a low-amplitude high-frequency acceleration corresponding to a gunshot sound and kick.

A second example of multi-sensorial activity type determination is swimming, wherein device 110 stores first-type sensor data that comprises moisture sensor data and second-type sensor data that comprises magnetic field data from a compass sensor. The reference data would comprise a swimming reference dataset, which would comprise moisture reference data and magnetic field reference data, to enable comparison with sensor data stored by device 110. Swimming may involve high moisture due to being immersed in water, and elliptical movements of an arm, to which device 110 may be attached, which may be detectable as periodically varying magnetic field data. In other words, the direction of the Earth's magnetic field may vary from the point of view of the magnetic compass sensor in a periodic way in the time series.

Overall, a determined, or derived, activity type may be considered an estimated activity type until the user has confirmed the determination is correct. In some embodiments, a few, for example two or three, most likely activity types may be presented to the user as estimated activity types for the user to choose the correct activity type from. Using two or more types of sensor data increases a likelihood the estimated activity type is correct.

A context process may be employed in deriving an estimated activity type based on sensor data. A context process may comprise first determining a context in which the sensor data has been produced. For example, the context process may comprise using the sensor data to determine the context, such as a user context, and then deriving an activity type within that context. For example, a context may comprise outdoor activity, and deriving an estimated activity type may comprise first determining, based on the sensor data, the user is in an outdoor context, selecting an outdoor-context machine readable instruction, and using the machine-readable instruction to differentiate between different outdoor-context activity types, such as jogging and orienteering. As another example, a context may comprise indoor activity, and deriving an estimated activity type may comprise first determining, based on the sensor data, the user is in an indoor context, selecting an indoor-context machine readable instruction, and using this machine-readable instruction to differentiate between different indoor activity types, such as 100 meter runs and wrestling.

The machine readable instruction may comprise, for example, a script, such as an executable or compilable script, an executable computer program, a software plugin or a non-executable computer-readable descriptor that enables device 110 to differentiate between at least two activity types within the determined context. The machine readable instruction may comprise indications as to which type or types of sensor data, and in which format, are to be used in deriving the activity type using the machine readable instruction.

Determining an outdoor context may comprise determining the sensor data indicates a wide range of geographic movement, indicating the user has roamed outdoors. Determining an indoor context may comprise determining the sensor data indicates a narrower range of geographic movement, indicating the user has remained within an small range during the activity session. Where temperature-type sensor data is available, a lower temperature may be associated with an outdoor activity and a higher temperature may be associated with an indoor activity. The temperature may be indicative of this in particular where the user is in a geographic area where winter, autumn or spring conditions cause an outdoor temperature to be lower than an indoor temperature. The geographic area may be available in positioning data.

Therefore, in some embodiments, deriving an estimated activity type is a two-phase process first comprising determining a context based on the sensor data, and then deriving an estimated activity type within that context, using a machine-readable instruction specific to that context. Selecting the context and/or the activity type within the context may comprise comparing sensor data, or processed sensor data, to reference data. The two-phase process may employ two types of reference data, context-type reference data and activity-type reference data, respectively.

The context process may adaptively learn, based on previous activity sessions recorded by a plurality of users, how to more accurately determine contexts and/or activity types. The determining of context may be based on the context-type reference data, for example, the context-type reference data being adaptively updated in dependence of the previous sessions recorded by the plurality of users. Adapting the context-type reference data may take place in a server, for example, the server being configured to provide updated context-type reference data to device such as device 110, or a personal computer associated therewith. A server may have access to information from the plurality of users, and high processing capability, and thus be more advantageously placed to update the context-type reference data than device 110, for example.

The two-phase process described above may be performed in a distributed fashion, wherein a user device, such as device 110, initially obtains sensor data of at least one, and in some embodiments at least two, types. This sensor data is used to compile a message, the message comprising the sensor data, at least in part, in raw or processed format, the message being transmitted from the user device to a back-end server. The server may use the sensor data in the message to determine a context in which device 110 seems to be in. This determining may be based on reference data, for example. The server may then provide a machine-readable instruction to the user device, to thereby enable the user device to derive an activity type within the context. This deriving may also be based, at least partly, on reference data. The reference data used in the server need not be the same as the reference data used in the user device.

Selection of the machine readable instruction in the server may be based, in addition to the sensor data, on capabilities of device 110. In particular, the machine readable instruction may be selected so that sensor data device 110 is capable of producing may be accepted as input to the machine readable instruction. To enable this selecting, the message transmitted from device 110 to the server may comprise an indication concerning device 110. Examples of such an indication include a model and make of device 110, a serial number of device 110 and an indication of sensor types disposed in device 110. Alternatively to being comprised in the same message, device 110 may provide the indication to the server in another message.

An advantage of the distributed two-phase process is that the user device need not be enabled to detect a great range of potential activity types with different characteristics. For example, the size of reference data used in the user device may be reduced by performing context detection in a server. The machine readable instruction may comprise, at least in part, the reference data used in the user device. As the size of reference data may be thus reduced, the user device may be built with less memory and/or the activity type derivation may consume less memory in the user device.

The machine readable instruction may enable detecting events within the context. An example is detecting a number of shots fired when hunting. Further examples include a number of times a down-hill slope has been skied down, a number of laps run on a track, a number of golf strokes played and, where applicable, initial velocities of golf balls immediately following a stroke. Further examples of detecting events are detecting a number of steps during running or strokes during swimming.

While an activity type is in general selectable within a context, an activity type may itself be seen as a context within which a further selection may be possible. For example, an initial context may comprise indoor activity, wherein an activity type may be identified as watersports. Within that activity type, swimming may be derived as an activity type. Further, breaststroke may be derived as an activity type where swimming is seen as a context. Therefore, while the terms "context" and "activity type" are employed herein for convenience, what is relevant is the hierarchical relationship between the two.

A user interface of device 110 may be modified based on the context or activity type. For example, where hunting is derived as an activity type, a user interface may display the number of detected shots. As another example, when swimming the number of laps, or the distance covered, may be displayed. In some embodiments, user interface adaptations have a hierarchical behaviour, such that initially, for example, an outdoor user interface is activated as a response to a determination that the current context is an outdoor context. When an activity type is identified within the context, the user interface may be further adapted to serve that specific activity type. In some embodiments, device 110 is configured to receive from a server user interface information to enable device 110 to adapt to a great number of situations, without a need to store all the user interface adaptations in device 110 beforehand.

In some embodiments, a server may transmit a request message to device 110, the request message being configured to cause device 110 to perform at least one measurement, such as a capturing of sensor data, for example, and to return a result of the measurement to the server. This way, the server may be enabled to detect what is occurring in the surroundings of device 110.

The machine readable instructions may be adapted by the server. For example, a user who first obtains a device 110 may initially be provided, responsive to the messages sent from device 110, with machine readable instructions that reflect an average user population. Thereafter, as the user engages in activity sessions, the machine readable instructions may be adapted to more accurately reflect use by this particular user. For example, limb length may affect periodical properties of sensor data captured while the user is swimming. To enable the adapting, the server may request sensor data from device 110, for example periodically, and compare sensor data so obtained to the machine readable instructions, to hone the instructions for future use with this particular user.

Figure 2:
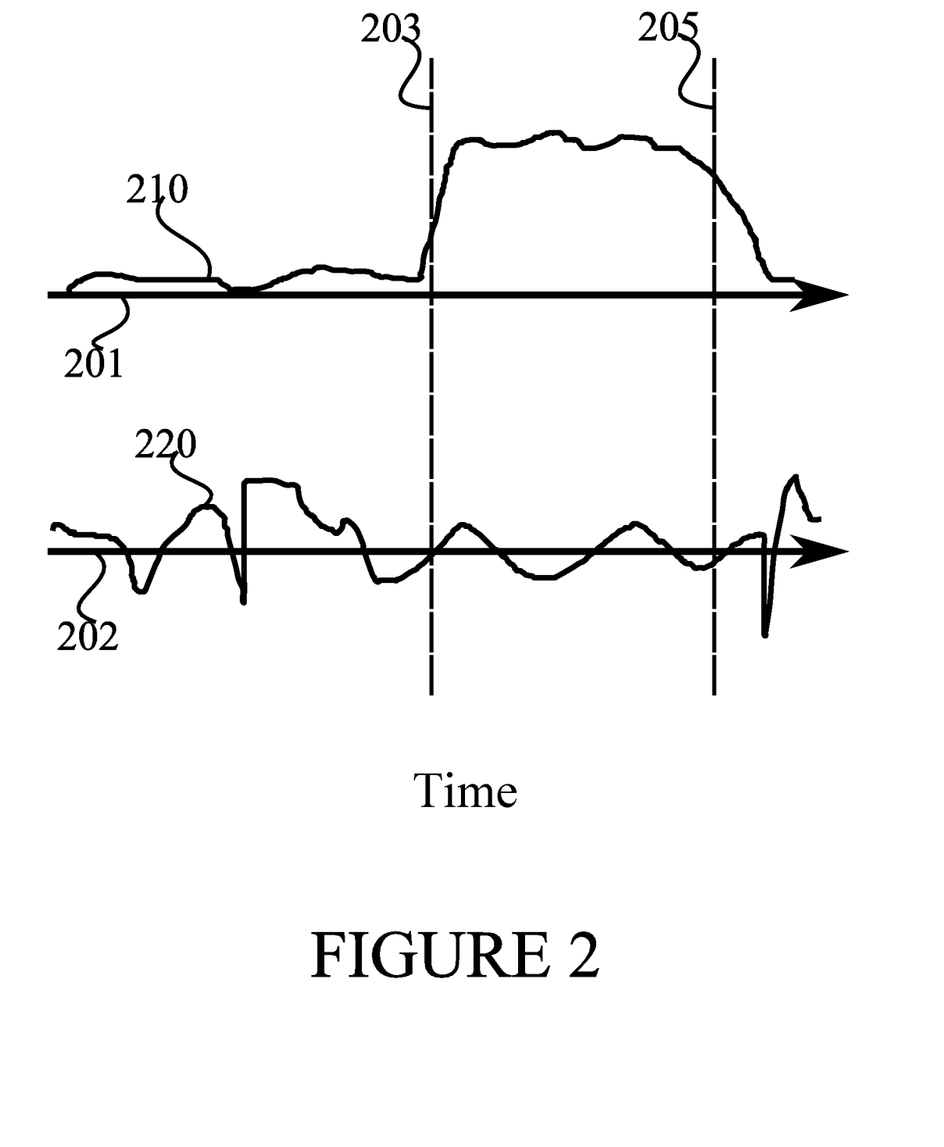
FIG. 2 illustrates an example multisensorial time series.

FIG. 2 illustrates an example multisensorial time series. On the upper axis, 201, is illustrated a moisture sensor time series 210 while the lower axis, 202, illustrates a time series 220 of deviation of magnetic north from an axis of device 110.

Moisture time series 210 displays an initial portion of low moisture, followed by a rapid increase of moisture that then remains at a relatively constant, elevated, level before beginning to decline, at a lower rate than the increase, as device 110 dries.

Magnetic deviation time series 220 displays an initial, erratic sequence of deviation changes owing to movement of the user as he operates a locker room lock, for example, followed by a period of approximately periodic movements, before an erratic sequence begins once more. The wavelength of the periodically repeating motion has been exaggerated in FIG. 2 to render the illustration clearer.

A swimming activity type may be determined as an estimated activity type, beginning from point 203 and ending in point 205 of the time series, based on a comparison with a reference dataset comprised in a machine readable instruction associated with a water sports context, for example. Via the reference dataset, swimming as an activity type may be associated with simultaneous high moisture and periodic movements.

Figure 2B:
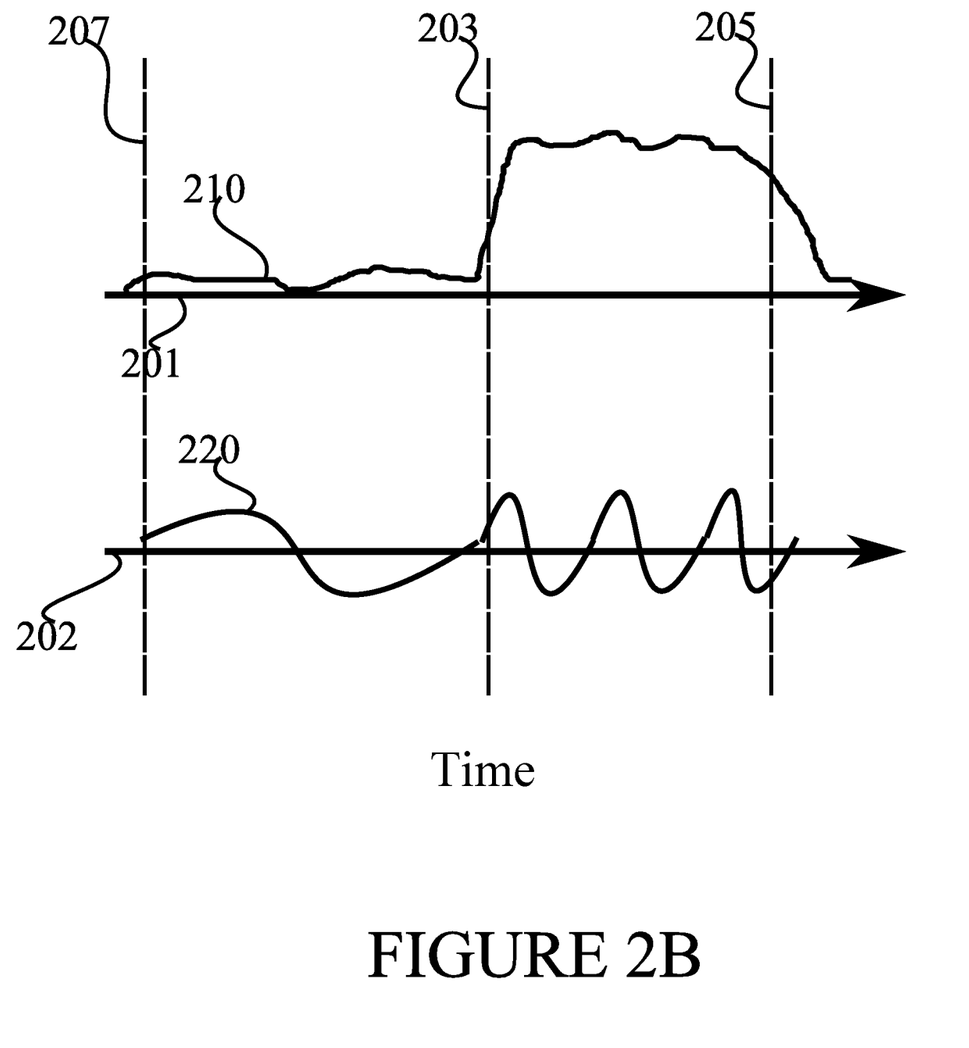
FIG. 2B illustrates a second example multisensorial time series.

FIG. 2B illustrates a second example multisensorial time series. In FIG. 2B, like numbering denotes like elements as in FIG. 2. Unlike in FIG. 2, not one but two activity sessions are determined in the time series of FIG. 2B. Namely, a cycling session is determined to start at beginning point 207 and to end at point 203, when the swimming session begins. Thus the compound activity session may relate to triathlon, for example. In cycling, moisture remains low, and magnetic deviation changes only slowly, for example as the user cycles in a velodrome.

Figure 3:
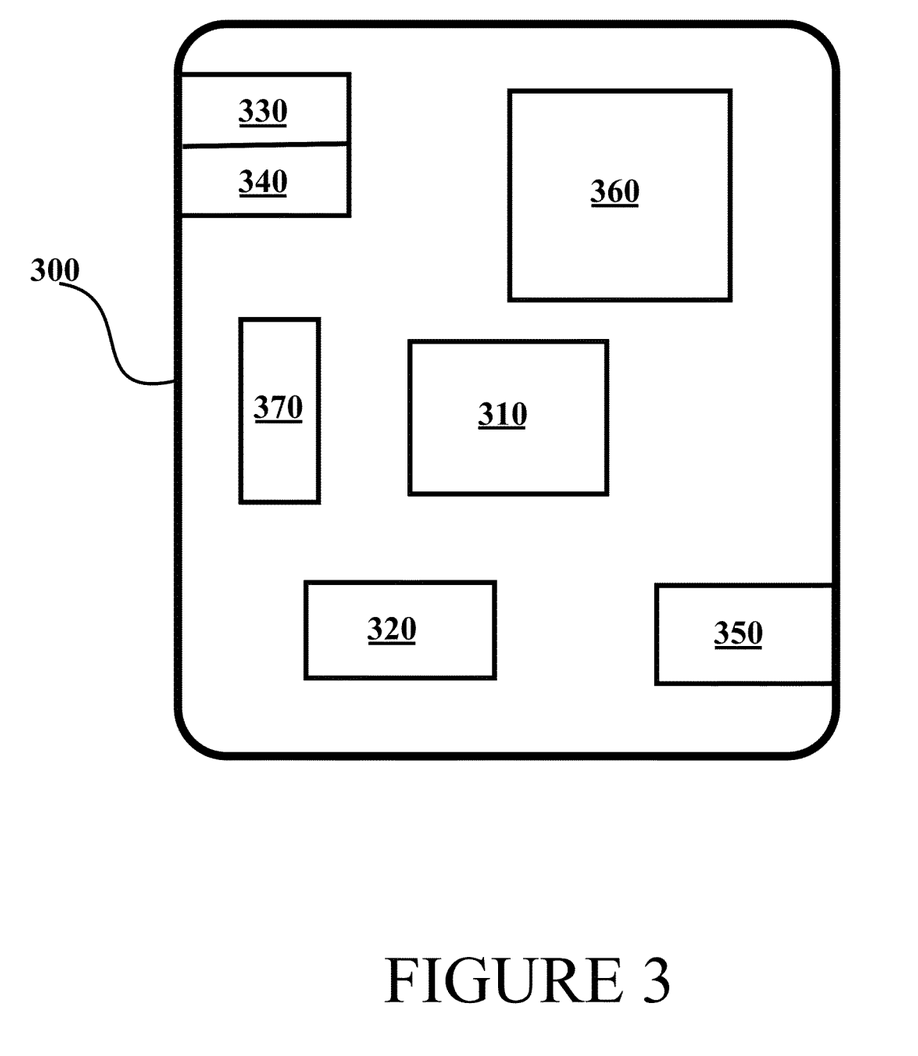
FIG. 3 illustrates an example apparatus capable of supporting at least some embodiments of the present invention.

FIG. 3 illustrates an example apparatus capable of supporting at least some embodiments of the present invention. Illustrated is device 300, which may comprise, for example, a mobile communication device such as mobile 110 of FIG. 1 or FIG. 2. Comprised in device 300 is processor 310, which may comprise, for example, a single- or multi-core processor wherein a single-core processor comprises one processing core and a multi-core processor comprises more than one processing core. Processor 310 may comprise more than one processor. A processing core may comprise, for example, a Cortex-A8 processing core manufactured by ARM Holdings or a Steamroller processing core produced by Advanced Micro Devices Corporation. Processor 310 may comprise at least one Qualcomm Snapdragon and/or Intel Atom processor. Processor 310 may comprise at least one application-specific integrated circuit, ASIC. Processor 310 may comprise at least one field-programmable gate array, FPGA. Processor 310 may be means for performing method steps in device 300. Processor 310 may be configured, at least in part by computer instructions, to perform actions.

Device 300 may comprise memory 320. Memory 320 may comprise random-access memory and/or permanent memory. Memory 320 may comprise at least one RAM chip. Memory 320 may comprise solid-state, magnetic, optical and/or holographic memory, for example. Memory 320 may be at least in part accessible to processor 310. Memory 320 may be at least in part comprised in processor 310. Memory 320 may be means for storing information. Memory 320 may comprise computer instructions that processor 310 is configured to execute. When computer instructions configured to cause processor 310 to perform certain actions are stored in memory 320, and device 300 overall is configured to run under the direction of processor 310 using computer instructions from memory 320, processor 310 and/or its at least one processing core may be considered to be configured to perform said certain actions. Memory 320 may be at least in part comprised in processor 310. Memory 320 may be at least in part external to device 300 but accessible to device 300.

Device 300 may comprise a transmitter 330. Device 300 may comprise a receiver 340. Transmitter 330 and receiver 340 may be configured to transmit and receive, respectively, information in accordance with at least one cellular or non-cellular standard. Transmitter 330 may comprise more than one transmitter. Receiver 340 may comprise more than one receiver. Transmitter 330 and/or receiver 340 may be configured to operate in accordance with global system for mobile communication, GSM, wideband code division multiple access, WCDMA, long term evolution, LTE, IS-95, wireless local area network, WLAN, Ethernet and/or worldwide interoperability for microwave access, WiMAX, standards, for example.

Device 300 may comprise a near-field communication, NFC, transceiver 350. NFC transceiver 350 may support at least one NFC technology, such as NFC, Bluetooth, Wibree or similar technologies.

Device 300 may comprise user interface, UI, 360. UI 360 may comprise at least one of a display, a keyboard, a touchscreen, a vibrator arranged to signal to a user by causing device 300 to vibrate, a speaker and a microphone. A user may be able to operate device 300 via UI 360, for example to manage activity sessions.

Device 300 may comprise or be arranged to accept a user identity module 370. User identity module 370 may comprise, for example, a subscriber identity module, SIM, card installable in device 300. A user identity module 370 may comprise information identifying a subscription of a user of device 300. A user identity module 370 may comprise cryptographic information usable to verify the identity of a user of device 300 and/or to facilitate encryption of communicated information and billing of the user of device 300 for communication effected via device 300.

Processor 310 may be furnished with a transmitter arranged to output information from processor 310, via electrical leads internal to device 300, to other devices comprised in device 300. Such a transmitter may comprise a serial bus transmitter arranged to, for example, output information via at least one electrical lead to memory 320 for storage therein. Alternatively to a serial bus, the transmitter may comprise a parallel bus transmitter. Likewise processor 310 may comprise a receiver arranged to receive information in processor 310, via electrical leads internal to device 300, from other devices comprised in device 300. Such a receiver may comprise a serial bus receiver arranged to, for example, receive information via at least one electrical lead from receiver 340 for processing in processor 310. Alternatively to a serial bus, the receiver may comprise a parallel bus receiver.

Device 300 may comprise further devices not illustrated in FIG. 3. For example, where device 300 comprises a smartphone, it may comprise at least one digital camera. Some devices 300 may comprise a back-facing camera and a front-facing camera, wherein the back-facing camera may be intended for digital photography and the front-facing camera for video telephony. Device 300 may comprise a fingerprint sensor arranged to authenticate, at least in part, a user of device 300. In some embodiments, device 300 lacks at least one device described above. For example, some devices 300 may lack a NFC transceiver 350 and/or user identity module 370.

Processor 310, memory 320, transmitter 330, receiver 340, NFC transceiver 350, UI 360 and/or user identity module 370 may be interconnected by electrical leads internal to device 300 in a multitude of different ways. For example, each of the aforementioned devices may be separately connected to a master bus internal to device 300, to allow for the devices to exchange information. However, as the skilled person will appreciate, this is only one example and depending on the embodiment various ways of interconnecting at least two of the aforementioned devices may be selected without departing from the scope of the present invention.

Figure 4:
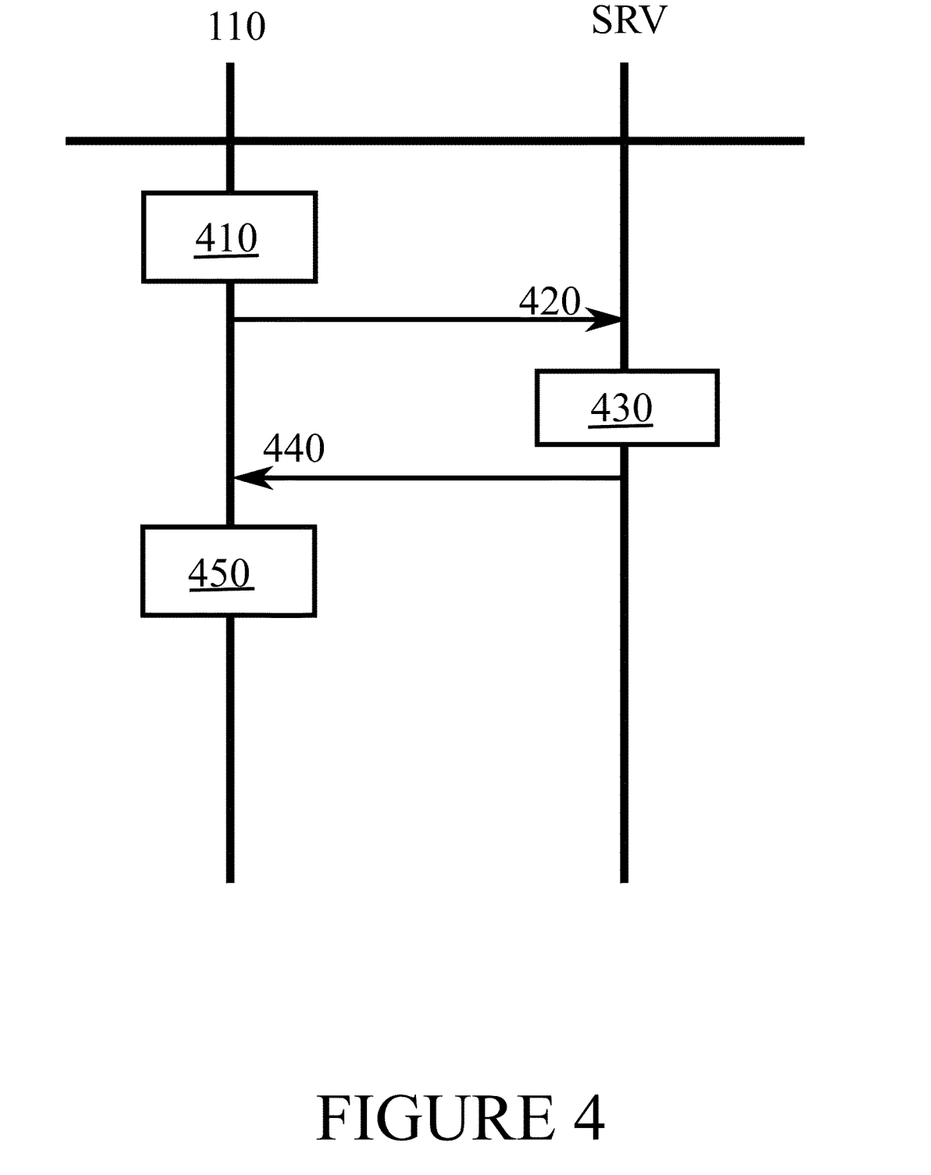
FIG. 4 illustrates signalling in accordance with at least some embodiments of the present invention.

FIG. 4 illustrates signalling in accordance with at least some embodiments of the present invention. On the vertical axes are disposed, on the left, device 110 of FIG. 1, and on the right, a server SRV. Time advances from the top toward the bottom. Initially, in phase 410, device 110 obtains sensor data from at least one, and in some embodiments from at least two sensors. The sensor data may comprise first-type sensor data and, in some embodiments, also second-type sensor data. The sensor or sensors may be comprised in device 110, for example. The sensor data may be stored in a time series, for example at a sampling frequency of 1 Hz, 10 Hz, 1 Khz or indeed another sampling interval. The sampling interval need not be the same in first-type sensor data and second-type sensor data.

Phase 410 may comprise one or more activity sessions of at least one activity type. Where multiple activity sessions are present, they may be of the same activity type or different activity types. The user need not, in at least some embodiments, indicate to device 110 that activity sessions are ongoing. During phase 410, device 110 may, but in some embodiments need not, identify activity types or sessions. The time series compiled during phase 410 may last 10 or 24 hours, for example. As a specific example, the time series may last from the previous time sensor data was downloaded from device 110 to another device, such as, for example, personal computer PC1.

In phase 420, the sensor data is provided, at least partly, in raw or processed format to server SRV. This phase may further comprise providing to server SRV optional activity and/or event reference data. The providing may proceed via base station 120, for example. The time series may be encrypted during downloading to protect the user's privacy.

In phase 430, server SRV may determine, based at least partly on the sensor data in the message of phase 420, a context and an associated machine readable instruction. Where activity and/or event reference data is provided in phase 420, that data may be employed in phase 430.

In phase 440 the machine readable instruction determined in phase 430 is provided to device 110, enabling, in phase 450, a derivation of an estimated activity type within that context, based on sensor data. The derivation of phase 450 may be based on sensor data that was included in the message of phase 420, or device 110 may capture new sensor data and use it, with the machine readable instruction, in the derivation of phase 450.

Figure 5:
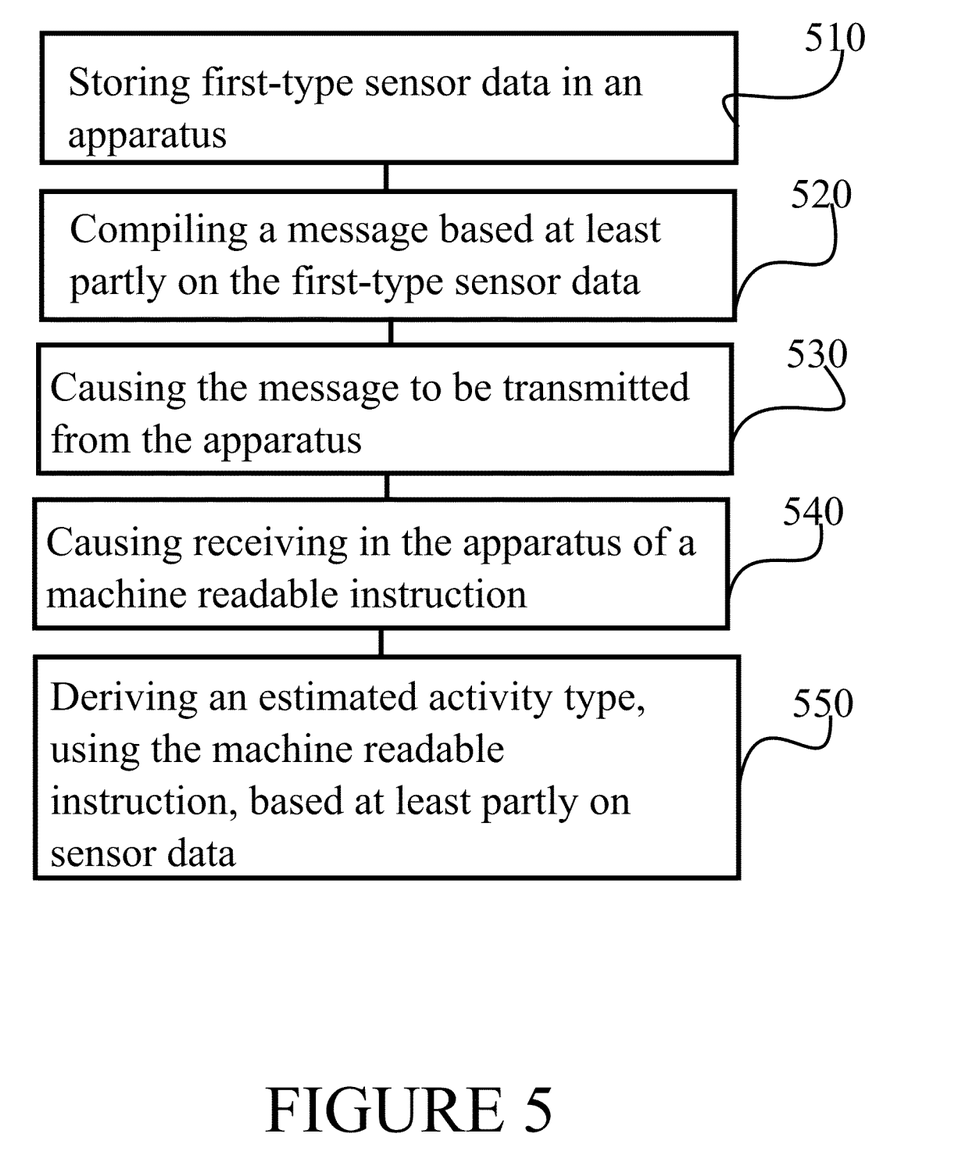
FIG. 5 is a flow graph of a method in accordance with at least some embodiments of the present invention.

FIG. 5 is a flow graph of a method in accordance with at least some embodiments of the present invention. The phases of the illustrated method may be performed in device 110, an auxiliary device or a personal computer, for example, or in a control device configured to control the functioning thereof, when implanted therein.

Phase 510 comprises storing first-type sensor data in an apparatus. Phase 520 comprises compiling a message based at least partly on the first-type sensor data. Phase 530 comprises causing the message to be transmitted from the apparatus. Phase 540 comprises causing receiving in the apparatus of a machine readable instruction, Finally, phase 550 comprises deriving an estimated activity type, using the machine readable instruction, based at least partly on sensor data. The message of phase 510 may comprise activity and/or event reference data.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in facilitating analysis of sensor data.

ACRONYMS LIST

GPS Global Positioning System
LTE Long Term Evolution
NFC Near-Field Communication
WCDMA Wideband Code Division Multiple Access
WiMAX worldwide interoperability for microwave access
WLAN Wireless local area network

| REFERENCE SIGNS LIST | |
|---|---|
| 110 | Device |
| 120 | Base Station |
| 130 | Network Node |
| 140 | Network |
| 150 | Satellite Constellation |
| 201, 202 | Axes in FIG. 2 |
| 203, 205, 207 | Activity session endpoints in FIG. 2 and FIG. 2B |
| 210, 220 | Sensor data time series in FIGS. 2 and 2B |
| 310-370 | Structure illustrated in FIG. 3 |
| 410-430 | Phases of the method of FIG. 4 |
| 510-530 | Phases of the method of FIG. 5 |

The invention claimed is:

1. A mobile user device comprising:
a memory configured to store first-type sensor data obtained during an activity session; and
at least one processing core configured to compile a message based at least partly on the first-type sensor data, to cause the message to be transmitted from the mobile user device to a server external to the mobile user device, to cause receiving, responsive to the message, in the mobile user device, from the server, of a machine readable instruction configured to differentiate an activity type in either an indoor or an outdoor activity context and comprising an executable program or an executable script, and to derive an estimated activity type, using the executable program or the executable script, based at least partly on sensor data, for the activity session which is ongoing or ended, wherein the activity type is selected from: rowing, paddling, cycling, jogging, walking, hunting, swimming, paragliding, orienteering, and running.

2. The mobile user device according to claim 1, wherein the machine readable instruction comprises a set of at least two machine-readable characteristics, wherein each of the machine-readable characteristics characterizes sensor data produced during a predefined activity type.

3. The mobile user device according to claim 1, wherein the at least one processing core is configured to derive the estimated activity type at least in part by comparing, using the executable program or the executable script, the first-type sensor data, or a processed form of the first-type sensor data, to reference data.

4. The mobile user device according to claim 1, wherein the first-type sensor data comprises acceleration sensor data.

5. The mobile user device according to claim 1, wherein the memory is further configured to store second-type sensor data, and wherein the at least one processing core is configured to derive the estimated activity type, using the executable program or the executable script, based at least in part on the second-type sensor data.

6. The mobile user device according to claim 4, wherein the second-type sensor data is of a different type than the first-type sensor data.

7. The mobile user device according to claim 5, wherein the second-type sensor data comprises at least one of: sound sensor data, microphone-derived data and vibration sensor data.

8. The mobile user device according to claim 5, wherein the at least one processing core is configured to derive the estimated activity type at least in part by comparing the second-type sensor data, or a processed form of the second-type sensor data, to reference data, the reference data comprising reference data of a first type and a second type.

9. The mobile user device according to claim 1, wherein the at least one processing core is configured to present the estimated activity type to a user for verification.

10. The mobile user device according to claim 1, wherein the at least one processing core is configured to cause the memory to store, in a sequence of estimated activity types, the estimated activity type and a second estimated activity type.

11. The mobile user device according to claim 1, wherein the at least one processing core is configured to cause the memory to delete the machine readable instruction responsive to a determination that an activity session has ended.

12. A server apparatus comprising at least one processing core, at least one memory including computer program code, the at least one memory and the computer program code being configured to, with the at least one processing core, cause the server apparatus at least to:
receive a message from a mobile user device external to the server apparatus, the message comprising information characterizing first-type sensor data obtained during an activity session;
determine, based at least partly on the first-type sensor data, an indoor or outdoor activity context, and
transmit, responsive to the message, to the mobile user device a machine-readable instruction configured to cause activity type determination in the determined indoor or outdoor activity context, wherein the machine readable instruction comprises an executable program or an executable script, wherein the activity type is selected from: rowing, paddling, cycling, jogging, walking, hunting, swimming, paragliding, orienteering, and running.

13. A method, comprising:
storing first-type sensor data obtained during an activity session in a mobile user device;
compiling a message based at least partly on the first-type sensor data;
causing the message to be transmitted from the mobile user device to a server external to the mobile user device;
causing receiving, responsive to the message, in the mobile user device, from the server, of a machine readable instruction configured to differentiate activity type in either an indoor or an outdoor activity context and comprising an executable program or an executable script, and
deriving an estimated activity type, using the executable program or the executable script, based at least partly on sensor data, for the activity session which is ongoing or ended, wherein the activity type is selected from: rowing, paddling, cycling, jogging, walking, hunting, swimming, paragliding, orienteering, and running.

14. The method according to claim 13, wherein the machine readable instruction comprises a set of at least two machine-readable characteristics, wherein each of the machine-readable characteristics characterizes sensor data produced during a predefined activity type.

15. The method according to claim 13, estimated activity type is derived at least in part by comparing, using the executable program or the executable script, the first-type sensor data, or a processed form of the first-type sensor data, to reference data.

16. The method according to claim 13, wherein the first-type sensor data comprises acceleration sensor data.

17. The method according to claim 13, further comprising storing second-type sensor data and wherein the estimated activity type is derived, using the executable program or the executable script, based at least in part on the second-type sensor data.

18. The method according to claim 17, wherein the second-type sensor data is of a different type than the first-type sensor data.

19. The method according to claim 17, wherein the second-type sensor data comprises at least one of: sound sensor data, microphone-derived data and vibration sensor data.

20. The method according to claim 17, wherein the estimated activity type is derived at least in part by comparing the second-type sensor data, or a processed form of the second-type sensor data, to reference data, the reference data comprising reference data of a first type and a second type.

21. The method according to claim 13, further comprising presenting the estimated activity type to a user for verification.

22. The method according to claim 13, further comprising storing, in a sequence of estimated activity types, the estimated activity type and a second estimated activity type.

23. A non-transitory computer readable medium having stored thereon a set of computer readable instructions that, when executed by at least one processor, cause a mobile user device to at least:
store first-type sensor data obtained during an activity session;

compile a message based at least partly on the first-type sensor data;

cause the message to be transmitted from the mobile user device to a server external to the mobile user device;

cause receiving, responsive to the message, in the mobile user device, from the server, of a machine readable instruction configured to differentiate activity type in either an indoor or an outdoor activity context comprising an executable program or an executable script, and derive an estimated activity type, using the executable program or the executable script, based at least partly on sensor data, for the activity session which is ongoing or ended, wherein the activity type is selected from: rowing, paddling, cycling, jogging, walking, hunting, swimming, paragliding, orienteering, and running.

24. A mobile user device for identification of user activity comprising:

a memory configured to store first-type sensor data relating to an activity session;

at least one processing core configured to:

compile a message based at least partly on the first-type sensor data, cause the message to be transmitted from the mobile user device to a server external to the mobile user device, cause receiving in the mobile user device from the server a response to the message as a machine readable instruction configured to differentiate activity type in either an indoor or an outdoor activity context and comprising at least two machine-readable characteristics, wherein each of the at least two machine-readable characteristics characterizes sensor data produced during a predefined activity type, the at least two machine-readable characteristics comprising reference data specific to a context where the mobile user device is operating, and derive an estimated activity type, using the reference data specific to the context, based at least partly on sensor data by comparing the sensor data to the reference data specific to the context, for the activity session which is ongoing or ended, wherein the activity type is selected from: rowing, paddling, cycling, jogging, walking, hunting, swimming, paragliding, orienteering, and running.

25. A non-transitory computer readable medium having stored thereon a set of computer readable instructions that, when executed by at least one processor, cause a mobile user device to at least:

store first-type sensor data relating to an activity session;

compile a message based at least partly on the first-type sensor data, cause the message to be transmitted from the mobile user device to a server external to the mobile user device, cause receiving in the mobile user device from the server a response to the message as a machine readable instruction configured to differentiate activity type in either an indoor or an outdoor activity context and comprising at least two machine-readable characteristics, wherein each of the at least two machine-readable characteristics characterizes sensor data produced during a predefined activity type, the at least two machine-readable characteristics comprising reference data specific to a context where the mobile user device is operating, and derive an estimated activity type, using the reference data specific to the context, based at least partly on sensor data by comparing the sensor data to the reference data specific to the context, for the activity session which is ongoing or ended, wherein the activity type is selected from: rowing, paddling, cycling, jogging, walking, hunting, swimming, paragliding, orienteering, and running.

* * * * *

UNITED STATES PATENT AND TRADEMARK OFFICE
CERTIFICATE OF CORRECTION

| | | |
|---|---|---|
| PATENT NO. | : 11,607,144 B2 | Page 1 of 1 |
| APPLICATION NO. | : 15/382763 | |
| DATED | : March 21, 2023 | |
| INVENTOR(S) | : Timo Eriksson, Mikko Martikka and Erik Lindman | |

It is certified that error appears in the above-identified patent and that said Letters Patent is hereby corrected as shown below:

On the Title Page

Item (30) Foreign Application Priority Data has been omitted.
Please insert:
-- (30) Foreign Application Priority Data
Dec. 21, 2015 (FI) ............................... 20155989
Dec. 21, 2015 (GB) ............................... 1522525 --

Signed and Sealed this
Twenty-seventh Day of August, 2024

Katherine Kelly Vidal
*Director of the United States Patent and Trademark Office*